US005552155A

United States Patent [19]
Bailey et al.

[11] Patent Number: 5,552,155
[45] Date of Patent: Sep. 3, 1996

[54] FUSOGENIC LIPSOMES AND METHODS FOR MAKING AND USING SAME

[75] Inventors: Austin L. Bailey; Pieter R. Cullis, both of Vancouver, Canada

[73] Assignee: The Liposome Company, Inc., Princeton, N.J.

[21] Appl. No.: 226,642

[22] Filed: Aug. 15, 1994

Related U.S. Application Data

[63] Continuation-in-part of Ser. No. 985,673, Dec. 4, 1992, abandoned.
[51] Int. Cl.⁶ .......................... A61K 9/127; A61K 9/133
[52] U.S. Cl. ...................................... 424/450; 428/402.2
[58] Field of Search .......................... 424/450; 436/829; 435/240.1, 240.26; 428/402.2

[56] References Cited

U.S. PATENT DOCUMENTS

| | | | |
|---|---|---|---|
| 4,522,803 | 6/1985 | Lenk et al. | 424/1.1 |
| 4,588,578 | 5/1986 | Fountain et al. | 424/1.1 |
| 4,873,089 | 10/1989 | Scotto | 424/450 |
| 4,885,172 | 12/1989 | Bally et al. | 424/417 |
| 4,975,282 | 12/1990 | Cullis et al. | 424/450 |
| 5,008,050 | 4/1991 | Cullis et al. | 264/4.3 |
| 5,030,453 | 7/1991 | Lenk et al. | 424/38 |
| 5,059,421 | 10/1991 | Loughrey et al. | 424/417 |
| 5,077,056 | 12/1991 | Bally et al. | 424/450 |
| 5,169,637 | 12/1992 | Lenk et al. | 424/450 |

FOREIGN PATENT DOCUMENTS

| | | | |
|---|---|---|---|
| 0127925 | 12/1984 | European Pat. Off. | A61K 49/02 |
| 0416527 | 3/1991 | European Pat. Off. | A61K 9/127 |
| 87/07530 | 12/1987 | WIPO | B01J 13/02 |
| 91/16024 | 10/1991 | WIPO | A61F 13/00 |
| 91/16880 | 11/1991 | WIPO | A61K 9/127 |

OTHER PUBLICATIONS

Bangham, et al., "Diffusion of Univalent Ions Across the Lamellae of Swollen Phospholipids", 1965; J. Mol. Biol., 13:238–252.

Cullis, et al., "Effects of fusogenic agent on membrane structure of erythrocyte ghosts and the mechanism of membrane fusion", Nature, 271:672–674, 1978.

Dimitriadis, et al., "Liposome–Mediate Ricin Toxicity in Ricin–Resistant Cells", FEBS Lett, 98(1):33–36, 1979.

Dimitriadis, "Translation of Rabbit Globin mRNA Introduced by Lipsomes into Mouse Lymphocytes", Nature, 274:923–924, 1978.

Eastman, et al., "Transbilayer Transport of Phosphatidic Acid in Response to Transmembrane pH Gradients", Biochem, 30: 1740–1745, 1991.

(List continued on next page.)

*Primary Examiner*—Gollamudi S. Kishore
*Attorney, Agent, or Firm*—Kenneth B. Rubin

[57] ABSTRACT

A liposome composition is provided which contains a liposome having: (i) an outermost lipid bilayer containing, in addition to a neutral, bilayer preferring lipid, a fusion-promoting effective amount of an ionizable lipid having a protonatable, cationic headgroup and an unsaturated acyl chain; and (ii) a compartment adjacent to the outermost lipid bilayer which contains an aqueous solution having a first pH. External to the liposome in the composition is an aqueous solution having a second pH. The first pH is less than the $pK_a$ of the ionizable lipid in the outermost lipid bilayer and the second pH is greater than the $pK_a$ of the ionizable lipid in the outermost lipid bilayer, such that there is a pH gradient across the outermost lipid bilayer and the ionizable lipid is accumulated in the inner monolayer of the outermost lipid bilayer in response to the gradient. The liposome can be fused in a controlled manner to another lipid bilayer, for example, the plasma membrane of a mammalian cell, by degrading the pH gradient when fusion is to occur, such that the ionizable lipid is neutral, evenly distributed in the outermost lipid bilayer and, fusogenic. Controlled fusion can be used to control the delivery of a biologically active agent entrapped in the liposome into a cell.

17 Claims, 10 Drawing Sheets

OTHER PUBLICATIONS

Eastman, et al., "Influence of Phospholipid Asymmetry on Fusion between Large Unilamellar Vesicles", Biochemistry 31: 42624268, 1992.

Fisher, et al., "Application of the Freeze–Fracture Technique to Natural Membranes", Methods Enzymol. 32: 35–44, 1974.

Fraley, et al., "Introduction of Liposome–encapsulated SV 40 DNA into Cells", J. Biol. Chem, 255(21), 10431–10435, 1980.

Hagins, et al. in: Vertebrate Photoreceptors, H. Barlow, et al., eds. Academic Press, New York, 1982, 97–139.

Hope, et al., "$CA^{2+}$ and pH Induced Fusion of Small Unilamellar Vesicles Consisting of phosphatidylethanolamine and Negatively Charged Phospholipids: A Freeze Fracture Study", Biochem, Biophys, Res. Comm. 110(1): 15–22, 1983.

Huang, et al., "Interactions of Phospholipid Vesicles with Murine Lymphocytes I. Vesicle–Cell Adsorption and Fusion as Alternate Pathways of Uptake", Membr. Biochem. 1:1–25 1978.

Huang, L. "Liposome–Cell Interactions In Vitro", in:Liposomes, M. Ostro, ed., Marcel Dekker, Inc., New York, (1983), 87–124.

Konopka, et al., "Enhancement of human immunodeficiency virus type 1 infection by cationic liposomes: the role of CD4, serum and liposome–cell interactions", J. Gen Virol, 72: 2685–2696, 1991.

Madden, et al., "The accumulaton of drugs within large unilamellar vesicles exhibiting a proton gradient: a survey", Chem. Phys. Lipids, 53:37–46, 1990.

Malone, et al., "Cationic Liposome–Mediated RNA Transfection", Proc. Natl. Acad. Sci, 86: 6077–6081, 1989.

Martin, et al., "Lipid Vesicle–Cell Interaction II. Induction of Cell Fusion" J. Cell Biol. 70, 506–514, 1976.

Martin, et al., "Lipid Vesicle–Cell Interaction III. Introduction of a New Antigenic Determinant Into Erythrocyte Membranes", J. Cell Biol, 70, 515–526, 1976.

Mayer, et al., "Vesicles of Variable Sizes Produced by a Rapid Extrusion Procedure", BBA, 858: 161–168, 1986.

Ostro, et al., "Parameters Affecting the Liposome–Mediated Insertion of RNA into Eucaryotic Cells In Vitro", Arch. Biochem. Biophys. 201:392–402, 1980.

Ostro, et al., "Evidence for Translation of Rabbit Globin mRNA after Liposome–Mediated Insertion into a Human Cell Line", Nature, 274: 921–923, 1978.

Pagano, et al., "Adhesion of Phospholipid Vesicles to Chinese Hamster Fibroblasts", J. Cell Biol. 74: 531–546, 1977.

Papahadjpoulos, et al. "Cellular Uptake of Cyclic Amp Captured Within Phospholipid Vesicles and Effect on Cell–Growth Behavior", BBA, 363: 404–418, 1974.

Papahadjopoulos, et al., "Use of Lipid Vesicles as Carriers to Introduce Actinomycin D into Resistant Tumor Cells", Cancer Res, 36: 2988–2994 (1976).

Papahadjopoulos, et al., "Phospholipid Model Membranes, Structural Characteristics of Hydrated Liquid Crystals", 1967; Biochim. Biophys. Acta, 135:624–638.

Poste, et al., "Drug–continuing lipid vesicles render drug–resistant tumour cells sensitive to actinomycin D", Nature, 261, 699–701, 1976.

Redelmeier, et al., "On the Mechanism of Transbilayer Transport of Phosphatidylglycerol in Response to Transmembrane pH Gradients", Biochem, 19: 3046–3053, 1990.

Senior, et al., "Interaction of positively–charged liposome with blood: implications for their application in vivo", BBA, 1070: 173–179, 1991.

Stamatatos, et al., "Interaction of Cationic Lipid Vesicles with Negatively Charged Phospholipid Vesicles and Biological Membranes", Biochem, 27: 3917–3925, 1988.

Szoka, et al., "Fluorescence Studies on the Mechanism of Liposome–Cell Interactions in Vitro", BBA, 600: 1–18, 1980.

Theoharides et al., "Secretion in Mast Cells Induced by Calcium Entrapped Within Phospholipid Vesicles", Science, 201: 1143–1145, 1978.

Weinstein, et al., "Liposome–Cell Interaction: Transfer and Intracellular Release of a Trapped Fluorescent Marker", Science, 195:489–492, 1977.

Weismann, et al., "Introduction of Enzymes, by Means of Liposomes, Into Non–Phagocytic Human Cells in Vitro", Biochem. Biophys. Acta, 498: 375–385, 1977.

Wilson, et al., "The Introduction of Poliovirus RNA into Cells via Lipid Vesicles (Liposomes)", Cell, 17: 77–84, 1979.

Das and Rand, Biochemistry 25: 2882–2889 (1986).

Duzgunes, et al., "Fusion of Liposomes Containing a novel Cationic Lipid, N–[2,3–(Dioleyloxy)propyl]–N,N,N–trimethylammonium: Induction by Multivalent Anions and Asymmetric Fusion with Acidic Phospholipid Vesicles", Biochem, 28: 9179–9184, 1989.

Gruner et al., Ann. Rev. Biophys. Comm. 14:211–238 (1985).

AL1

AL2

AL3 R=CH$_3$

AL4 R=(CH$_2$)$_2$CH$_3$

AL5 R=(CH$_2$)$_8$CH$_3$

AL6

FUSOGENIC LIPSOMES AND METHODS FOR MAKING AND USING SAME

This application is a continuation-in-part of U.S. Ser. No. 985,673, filed Dec. 4, 1992, now abandoned and is directed to fusogenic liposomes, methods of making such liposomes, and methods of controlling the fusion of the liposomes to other lipid bilayers.

Liposomes are self-assembling structures comprising one or more bilayers of amphipathic lipid molecules each of which encloses an internal aqueous volume. The amphipathic lipid molecules which make up lipid bilayers comprise a polar (hydrophilic) headgroup region covalently linked to one or two non-polar (hydrophobic) acyl chains. It is believed that the energetically unfavorable contact between the hydrophobic acyl chains and the aqueous solution surrounding the lipid molecules causes them to rearrange such that the polar headgroups are oriented towards the aqueous solution while the acyl chains orient towards the interior of the bilayer. The net result is an energetically stable lipid bilayer structure comprising two opposing monolayers, in which the acyl chains are effectively shielded from coming into contact with the aqueous medium.

Liposomes may be produced by a variety of methods. Bangham's procedure (J. Mol. Biol. 13:238–252 (1965)) produces "ordinary" multilamellar liposomes (MLVs). "Ordinary" MLVs can have unequal solute distribution amongst their aqueous compartments and thereby, osmotic stress between compartments. Lenk et al. (U.S. Pat. Nos. 4,522,803, 5,030,453 and 5,169,637), Fountain et al. (U.S. Pat. No. 4,588,578) and Cullis et al. (U.S. Pat. No. 4,975,282) disclose methods for producing multilamellar liposomes having substantially equal distribution of an entrapped solute in each of their aqueous compartments, that is, substantially equal interlamellar solute distribution. Having substantially equal interlamellar solute distribution means that there will be less osmotic stress amongst the aqueous compartments of these MLVs, which will therefore generally be more stable than ordinary MLVs. Unilamellar liposomes can be produced from MLVs by sonication (see Paphadjopoulos et al. (1968)) or extrusion (Cullis et al. (U.S. Pat. No. 5,008,050) and Loughrey et al. (U.S. Pat. No. 5,059,421)).

Liposomes can be loaded with bioactive agents passively, that is, by solubilizing the molecule in the medium in which the liposomes are formed, in the case of water-soluble agents, or adding lipid-soluble agents to the lipid solutions from which the liposomes are made. Ionizable bioactive agents can also be loaded into liposomes by establishing an electrochemical potential gradient across the liposomal membrane and then adding the agent to the medium external to the liposome (see Bally et al., U.S. Pat. No. 5,077,056).

Drugs entrapped within liposomes can have an enhanced therapeutic index by reducing toxicity, increasing efficacy, or both. Furthermore, liposomes, like other particulate matter in the circulation, are taken up by phagocytic cells of the reticuloendothelial system in tissues having sinusoidal capillaries, and are thereby often directed to the sites of intracellular infections.

Fusion of biological membranes is a key process in a variety of cellular transport functions, including endocytosis, fertilization and the intracellular trafficking of proteins. Fusion of liposomes with cells is defined as the unification of the outermost bilayer of the liposome with the plasma membrane of the cell (see Huang (1983)). For fusion to occur, the lipids of the outermost lipid bilayer must mix with lipids of the cell's plasma membrane. The proposed mechanism by which fusion occurs between lipid membranes involves neutralization of the charged headgroups, resulting in an effective change in the geometry of the lipid species producing nonbilayer-preferring structures. These in turn give rise to micelles or other defects in the bilayer which act as nucleation sites for membrane fusion (Cullis and Hope (1978)).

Studies employing liposomes have demonstrated a correlation between the tendency of liposomes to fuse and the propensity of component lipids to adopt non-bilayer phases, such as the hexagonal $H_{II}$ phase, leading to the suggestion that non-bilayer structures, for example, inverted micelles or other bilayer defects, are intermediary structures in fusion events (see, for example, Cullis et al. (1978)). Lipid composition is believed to contribute to the tendency of liposomes to adopt non-bilayer structures (see, for example, Martin and MacDonald (1976); Martin and MacDonald (1976); Weismann et al. (1977)). For example, membranes containing negatively charged phospholipids (for example, phosphatidic acid (PA), phosphatidylserine (PS), etc.) have been shown to fuse in the presence of divalent cations such as $Ca^{++}$ (Hope et al. (1983)). Synthetic cationic lipids have been shown to undergo fusion using high concentrations of negatively charged counterions (Düzgünes et al. (1989)). Unsaturated diglycerides are also believed to be potent fusogens (Das and Rand (1986)). Furthermore, uncharged lipids are believed to be more readily able to adopt non-bilayer structures, and hence, to be more fusogenic, than are their charged forms (see, for example, Gruner et al. (1985)).

Cationic lipids have proven useful in increasing the efficiency of mammalian cell transfection (see, for example, Malone et al. (1989); Konopka et al. (1991)). The extension of these applications to the in vivo delivery of liposomally encapsulated materials has encountered problems of cellular toxicity, hemolysis and accelerated clotting responses caused by cationic lipids (Senior et al. (1991)). These effects appear to occur above a threshold level of positive charge, and do not appear to be largely dependent on the nature of the cationic species. Although, the toxic effects of cationic species are being challenged by the synthesis of novel cationic head groups, they remain largely unsolved. The potential applications of these lipids to targeted drug delivery make the reduction of the toxic side effects, by reducing cationic concentration, and the ability to control the fusogenic nature *in vivo* of these compounds, desirable.

Fusion between vesicle populations bearing opposite charges has also been demonstrated (Stamatatos et al. (1988)). Controlled fusion of liposomes using induced lipid asymmetry has been previously addressed (Eastman et al. (1991); Eastman et al. (1992); Redelmeier et al. (1990)). However, these references are directed to the use of anionic ionizable lipids; the pH gradient used to transport the anionic lipid is the reverse of that for the loading of cationic drugs into liposomes (see Bally et al., U.S. Pat. No. 5,077,056). Controlled fusion of these drug-loaded liposomes would be better served by an analogous fusogenic, cationic lipid.

Fusion of liposomes with biological membranes can deliver the contents of the liposomes into cells. The injection of the aqueous content of liposomes into the cytoplasm has been shown by the fluorescence dequenching of carboxyfluorescein (Weinstein et al. (1977); Huang et al. (1978). Other reports have also shown that biologically active materials (for example, cAMP, ricin, actinomycin D, $Ca^{++}$, mRNA, and viruses and viral genomes) incorporated into liposomes can be introduced into the interiors of cells (see, for example, Paphadjopoulos et al. (1974); Dimitriadis and Butters (1979); Theoharides and Douglas (1978); Ostro et al. (1978); Dimitriadis (1978); Wilson et al. (1979); Fraley et al. (1980)) by way of fusion between liposomal lipid bilayers and cellular membranes. However, other studies suggest that fusion is not a major mechanism of liposomal interactions with cells (see, for example, Szoka et al. (1980); Hagins and Yoshikami (1982); Pagano and Takeichi (1977)).

The contents of the above-cited publications are incorporated herein by reference. None of these publications disclose a liposome composition containing a liposome having an ionizable, cationic lipid and a transmembrane pH gradient, nor do they disclose use of such a gradient to control the transbilayer distribution, and hence, fusogenic potential, of the ionizable lipid.

SUMMARY OF THE INVENTION

This invention provides a liposome composition which comprises a liposome having: (i) an outermost lipid bilayer comprising a neutral, bilayer-preferring lipid and a fusion-promoting effective amount of an ionizable lipid having a protonatable, cationic headgroup and an unsaturated acyl chain; and (ii) a compartment adjacent to the outermost lipid bilayer comprising an aqueous solution having a first pH. The composition also comprises an aqueous solution external to the liposome having a second pH, wherein the first pH is less than the $pK_a$ of the ionizable lipid in the outermost lipid bilayer and the second pH is greater than the $pK_a$ of the ionizable lipid in the outermost lipid bilayer, whereby there is a pH gradient across the outermost lipid bilayer and whereby the ionizable lipid is accumulated in the inner monolayer of the outermost lipid bilayer.

The liposome can be a unilamellar liposome; the unilamellar liposome is preferably a large unilamellar liposome. The liposome can also be a multilamellar liposome; preferably, the multilamellar liposome comprises a solute entrapped in its aqueous compartments, wherein the concentration of the solute in each of the aqueous compartments of the multilamellar liposome is substantially equal. The internal aqueous solution in the liposome is preferably an aqueous buffer, more preferably, an aqueous buffer having a pH of about 4.0. Preferably, the aqueous pH 4.0 buffer is a citrate buffer.

The fusion-promoting effective amount of the ionizable lipid is typically an amount sufficient to establish a concentration of the ionizable lipid in the outermost lipid bilayer of the liposome of from about 1 mole percent of the ionizable lipid to about 20 mole percent; preferably within this range, the preferred fusion-promoting effective amount of the ionizable lipid in the outermost lipid bilayer is an amount sufficient to establish a concentration of the ionizable lipid in the outermost lipid bilayer of from about 5 mole percent to about 10 mole percent of the ionizable lipid.

The cationic headgroup of the ionizable lipid is preferably an amino group, and the unsaturated acyl chain is preferably an oleic acid chain. In a presently preferred embodiment of the invention, the cationic headgroup is an amino group, the unsaturated acyl chain is an oleic acid chain and the ionizable lipid is 1-N,N-dimethylamino dioleoyl propane (AL-1). The ionizable lipid can also be selected from the group consisting of ±-oleoyl-2-hydroxy-3-N,N-dimethylamino propane (AL-2), asymmetric ±-1,2-diacyl-3-N,N-dimethylamino propane (AL-3-AL-5) and ±-1,2-didecanoyl-1-N,N,-dimethylamino propane (AL-6). More preferably, presently, the ionizable lipid is 1-N,N-dimethylamino dioleoyl propane (AL-1).

The aqueous solution external to the liposome is an aqueous buffer having a pH which is greater than the $pK_a$ of the ionizable lipid in the outermost lipid bilayer. Preferably, when the ionizable lipid is AL-1, the pH of the external aqueous buffer is about 7.5. The liposome can further comprise a neutral, non-bilayer-preferring lipid, for example, dioleoyl phosphatidylethanolamine (DOPE). The liposome can comprise a biologically active agent, which is typically a nucleic acid, an antimicrobial agent, an anticancer agent or an anti-inflammatory agent. The aqueous solution external to the liposome can be a pharmaceutically acceptable aqueous solution, and the liposome composition can be a pharmaceutical composition.

This invention also provides a dehydrated liposome having an outermost lipid bilayer comprising a neutral, bilayer-preferring lipid and a fusion-promoting effective amount of an ionizable lipid having a cationic headgroup and unsaturated acyl chains, wherein the ionizable lipid is accumulated in the inner monolayer of the outermost lipid bilayer.

Further provided herein is a method of controlling the fusion of a liposome to a second lipid bilayer. The method comprises preparing the liposome in an aqueous solution, wherein the liposome comprises: (1) an outermost lipid bilayer comprising a neutral, bilayer-preferring lipid and a fusion-promoting effective amount of an ionizable lipid having a protonatable, cationic headgroup and an unsaturated acyl chain; and (2) a compartment adjacent to the outermost lipid bilayer comprising the aqueous solution. The pH of the aqueous solution is less than the $pK_a$ of the ionizable lipid in the outermost lipid bilayer. The pH of the aqueous solution external to the liposome is then raised above the $pK_a$ of the ionizable lipid in the outermost lipid bilayer, thereby establishing a pH gradient across the outermost lipid bilayer. The ionizable lipid is accumulated in the inner monolayer of the outermost lipid bilayer in response to the pH gradient. The pH gradient is degraded when fusion of the liposome to the second lipid bilayer is to occur, so that the liposome fuses to the second lipid bilayer.

The liposome used in the method of this invention can comprise a biologically active agent, which is typically a nucleic acid, antimicrobial agent, anticancer agent or anti-inflammatory agent. The second lipid bilayer to which the liposome is fused in a controlled manner is preferably the plasma membrane of a cell, most preferably, the plasma membrane of a mammalian cell.

This invention provides a method of introducing a biologically active agent into a cell which comprises preparing a liposome comprising the agent in an aqueous solution so that the aqueous solution is internal and external to the liposome. The liposome comprises an outermost lipid bilayer which comprises a neutral, bilayer-preferring lipid and an ionizable lipid having a cationic headgroup and unsaturated acyl chains. The pH of the internal aqueous solution is less than the pKa of the ionizable lipid in the outermost lipid bilayer. The pH of the external aqueous medium is increased above the pKa of the ionizable lipid in the outermost lipid bilayer so that there is a pH gradient across the outermost lipid bilayer and the ionizable lipid is then accumulated in the inner monolayer of the outermost lipid bilayer. The pH of the internal aqueous solution is increased above the $pK_a$ of the ionizable lipid in the outermost lipid bilayer prior to contacting the cell with the liposome. Preferably, the cell is a mammalian cell

Mole % AL-1; y-axis: fluorescence. Error bars are smaller than symbols where not indicated. (B) Fluorescence traces showing the effect of a pH gradient and 10 mole % AL-1 on TNS fluorescence of EPC/Chol (55:45)liposomes. Liposomes were prepared with 0 mole % AL-1 (lower traces) or 10 mole % AL-1 (upper traces). Internal buffer was either 300 mM citrate, pH 4.0 (lower traces) or 20 mM HEPES buffer, pH 7.5 (upper trace). x-axis: Time (seconds); y-axis: fluorescence.

Figure 2:
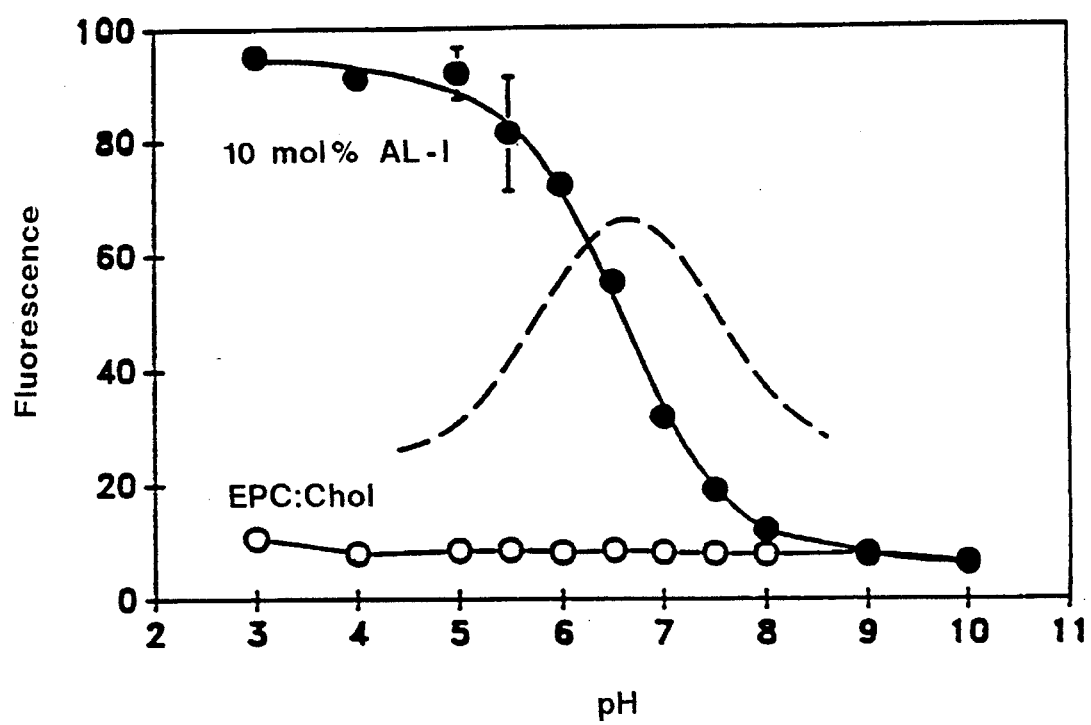

FIG. 2. Effect of pH on the fluorescence of EPC/Chol (55:45) Liposomes. Data shown represent mean values from the duplicate experiments, and error bars are smaller than symbols where not otherwise indicated. The dashed line is the inverted first derivative of the titration curve and its maximum indicates a $pK_a$ of 6.7 for AL-1 in the lipid bilayer. x-axis: pH; y-axis: $\%\Delta F/\Delta F_{max}$.

Figure 3:
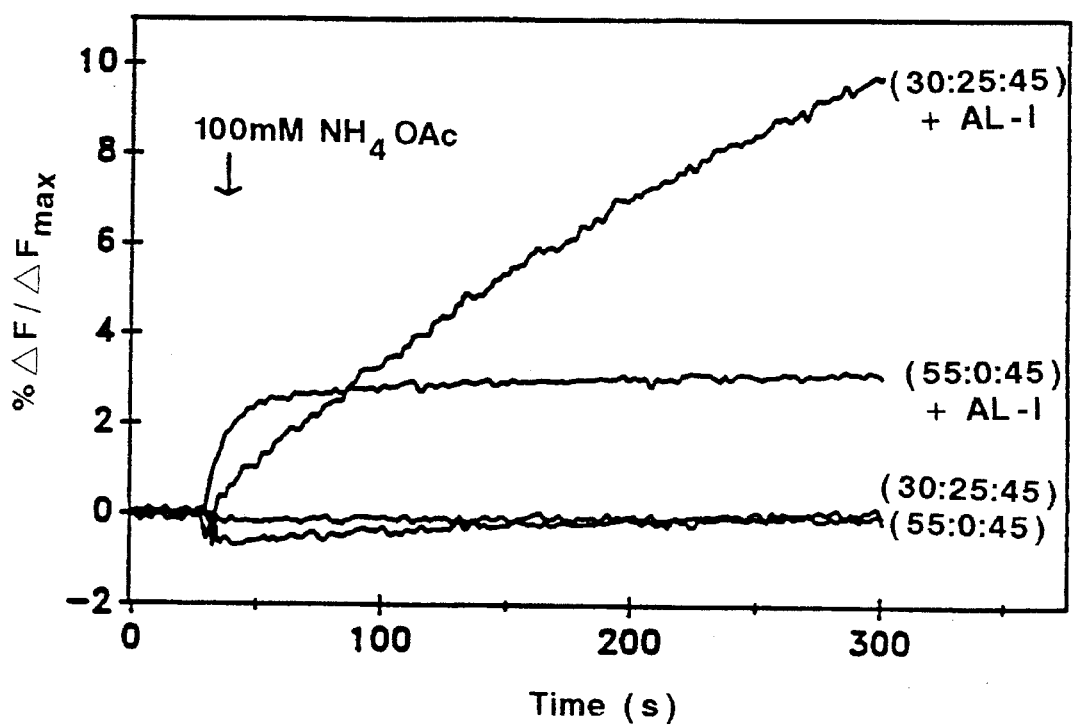

FIG. 3. Effect of 0 and 10 mole % AL-1 on the fusion of EPC/Chol (55:45) liposomes and EPC/DOPE/Chol (30:25:55)liposomes by RET fluorescent probe dilution. Data shown are different traces of runs with, and without, dissipation of the pH gradient, where $\Delta F_{max}$ was determined by the addition of Triton X-100 to a final concentration of 0.8 mM. x-axis: time (seconds); y-axis: fluorescence.

Figure 4:
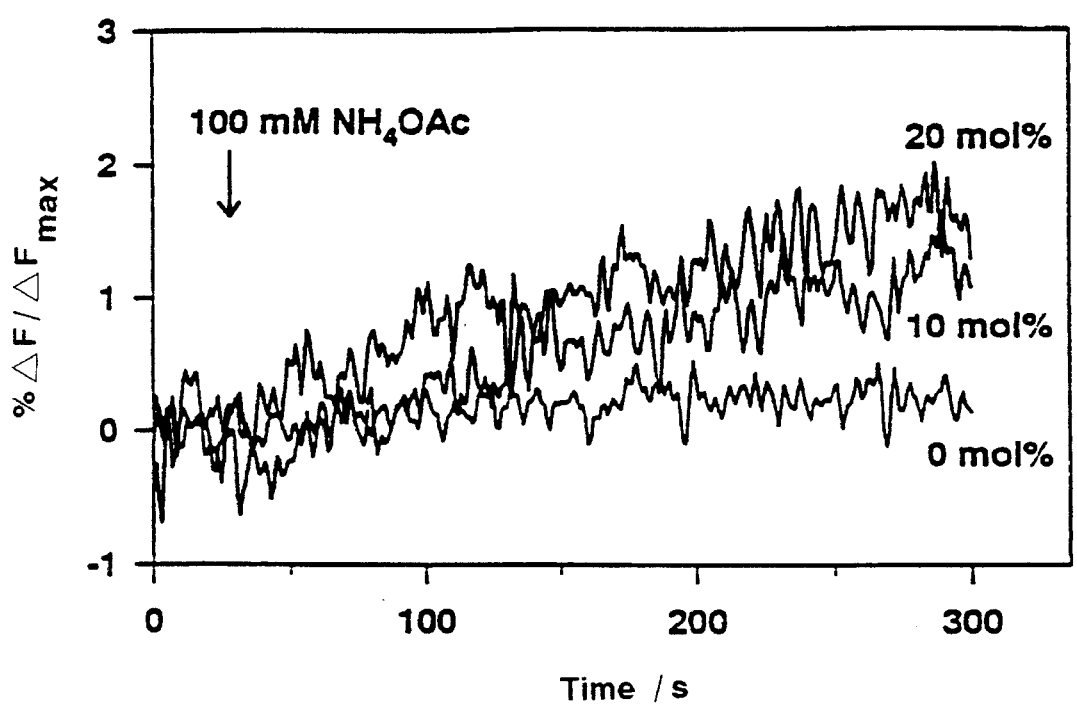

FIG. 4. Effect of AL-1 Concentration (0–20 Mole %) on Fusion of EPC/Chol (55:45, mole/mole) Liposomes by RET Fluorescent Probe Dilution. x-axis: Time (seconds); y-axis: fluorescence.

Figure 5:
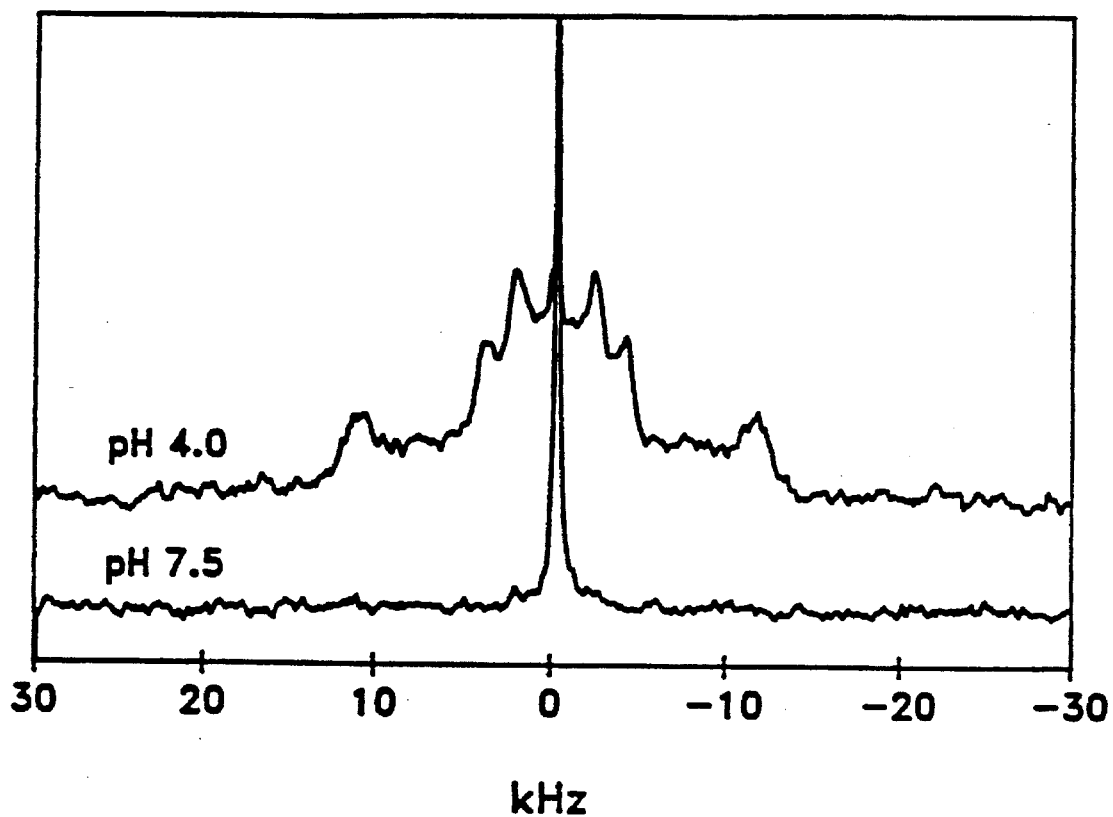

FIG. 5. $^2$H-NMR spectra of MLVs prepared with 10 mole % AL-1-$d_4$ in EPC/Chol (55:45) in 100 mM ammonium acetate at pH 4.0 and pH 7.5. x-axis: Frequency (kHz).

Figure 6:
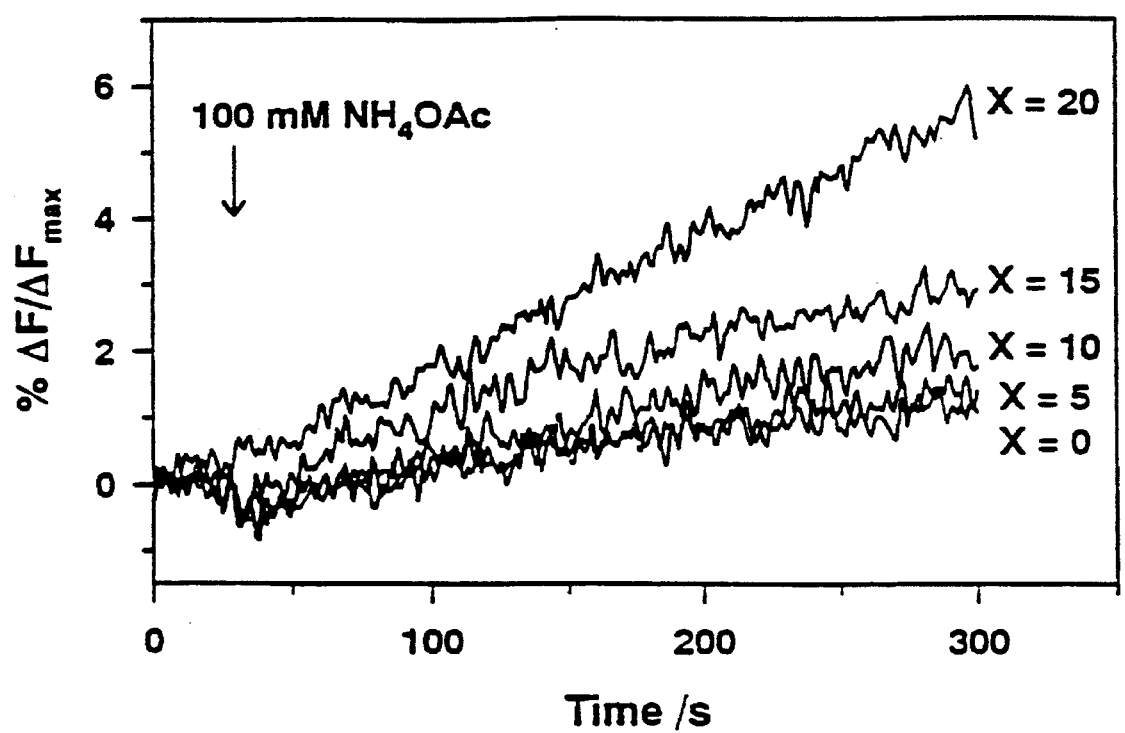

FIG. 6. Effect of DOPE Concentration on Fusion Rates of Liposomes Containing AL-1. Fusion assays were carried out as described above x-axis: Time (seconds); y-axis: $\%\Delta F/\Delta F_{max}$.

Figure 7:
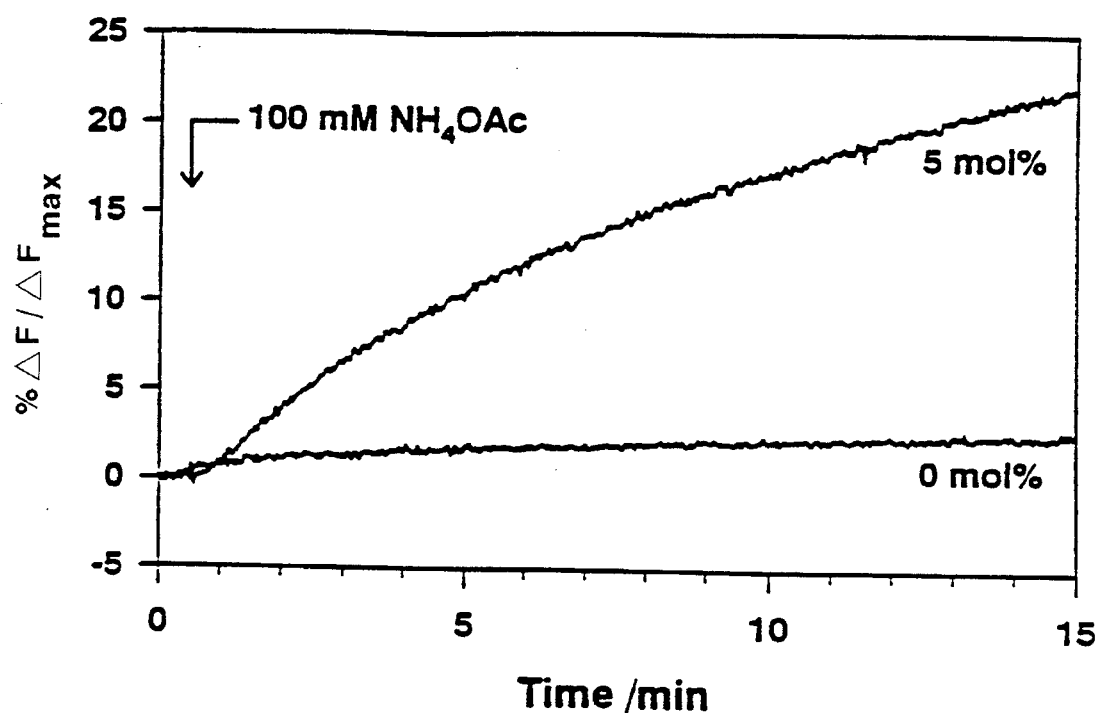

FIG. 7. Fusion of Liposomes Consisting of 0 and 5 mole % AL-1 and EPC/Chol/DOPE (35:20:45, mole/mole). x-axis: Time (seconds); y-axis:: $\%\Delta F/\Delta F_{max}$.

FIG. 8. A: $^2$H-NMR (x-axis: frequency (kHz)), B: $^{31}$P-NMR (x-axis: δ/ppm) spectra of freeze-thawed MLVs prepared with 5 mole % AL-1-$d_4$ in EPC/DOPE/Chol Liposomes, buffered with 20 mM HEPES, 20 mM sodium acetate, 150 mM NaCl, at pH 4.0 and pH 7.5.

Figure 9:
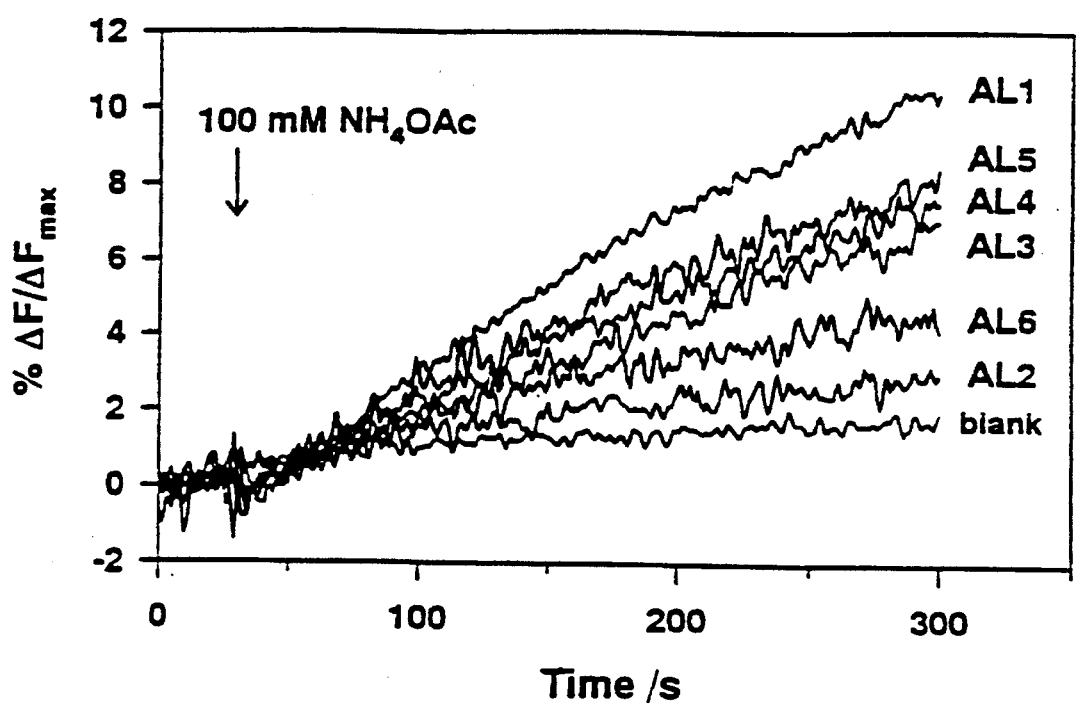

FIG. 9. Effect of Aminolipid Structure on Fusion of EPC/Chol/DOPE (35:20:45) Liposomes by RET Fluorescence Probe Dilution. Traces (uppermost-lowermost): AL-1, AL-5, AL-4, AL-3, AL-6, AL-2 and blank. x-axis: Time (seconds); y-axis: $\%\Delta F/\Delta F_{max}$.

Figure 10:
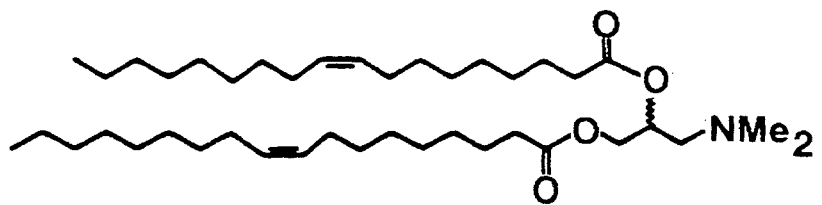
Figure 10:
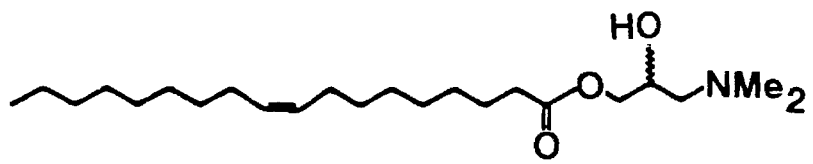
Figure 10:
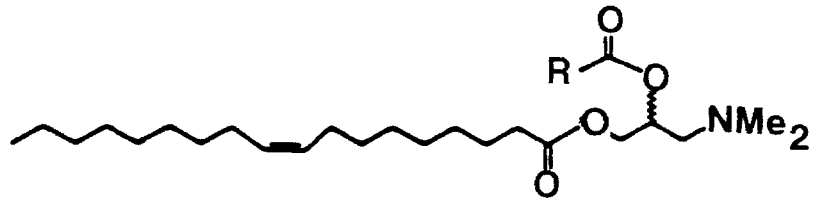
Figure 10:
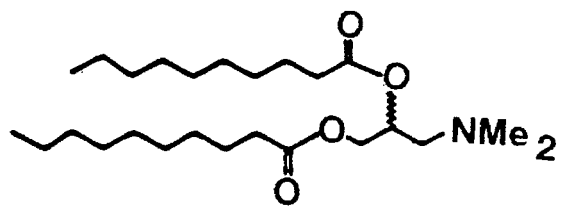

FIG. 10. Synthetic Aminolipid Structures.

DETAILED DESCRIPTION OF THE INVENTION

This invention provides a liposome composition which comprises a liposome having: (i) an outermost lipid bilayer comprising a neutral, bilayer-preferring lipid and a fusion-promoting effective amount of an ionizable lipid comprising a protonatable, cationic headgroup and an unsaturated acyl chain; (ii) a compartment adjacent to the outermost lipid bilayer which comprises an aqueous solution (the "internal aqueous solution") having a first pH. The composition also comprises an aqueous solution external to the liposome having a second pH. The first pH is less than the pKa of the ionizable lipid in the outermost lipid bilayer and the second pH is greater than the pKa of the ionizable lipid in the outermost lipid bilayer, whereby there is a pH gradient across the outermost lipid bilayer, and the ionizable lipid is accumulated in the inner monolayer of the outermost lipid bilayer in response to the pH gradient.

Liposomes are self-assembling structures comprising one or more lipid bilayers, each of which surrounds a compartment comprising an aqueous solution. Each bilayer of the liposome is formed by the association of amphipathic lipid molecules such that their polar, hydrophilic headgroups are oriented towards the surrounding aqueous solution while the hydrophobic acyl chains are oriented towards the interior of the bilayer, and away from the surrounding aqueous phase. Consequently, lipid bilayers have both inner and outer monolayers of lipid molecules.

A unilamellar liposome has one lipid bilayer; multilamellar liposomes have more than one lipid bilayer. The liposome used in the liposome composition of this invention can be a unilamellar liposome, preferably, a large unilamellar liposome (LUV). An LUV is a unilamellar liposome having a diameter of greater than about 50 nm. The liposome can also be a multilamellar liposome (MLV), preferably, the MLV comprises a solute entrapped in its aqueous compartments, wherein the concentration of the solute in each of the aqueous compartments is substantially equal. Such MLVs have substantially equal interlamellar solute distribution. Typically, the liposomes of this invention have sizes, as measured by their diameters, of about 5000 nm or less. Liposome size can be determined by techniques, for example, quasi-electric light scattering, that are well known to ordinarily skilled artisans and are readily practiced by them.

The "outermost lipid bilayer" of a unilamellar liposome is the single lipid bilayer of the liposome; in a multilamellar liposome, the "outermost lipid bilayer" is the lipid bilayer in contact with the aqueous solution external to the liposome (the "external aqueous solution"). Liposomes can be prepared by a variety of methods (see, for example, Cullis et al. (1987), Bangham et al. (1965), Lenk et al. (U.S. Pat. Nos. 4,522,803, 5,030,453 and 5,169,637, Fountain et al. (U.S. Pat. No. 4,588,578) and Cullis et al. (U.S. Pat. No. 4,975,282)).

The liposome has an outermost lipid bilayer which comprises a neutral, bilayer-preferring lipid comprising a neutral (uncharged, non-cationic/non-anionic, nonprotonatable) headgroup and bilayer-preferring acyl chains. These acyl chains, which can be symmetric or asymmetric (of unequal length, or number of carbon atoms), saturated (no double bonds between adjacent carbon atoms) or unsaturated (one or more double bonds between adjacent carbon atoms), are believed to inhibit or prevent phase separation of nonbilayer-preferring lipids in the bilayer, generally by adopting compatible acyl chain packing with the acyl chains of the other lipids incorporated in the bilayer. Bilayer-preferring lipids can form stable lipid bilayers on their own, as well as in connection with other bilayer-preferring lipids and with nonbilayer-preferring lipids. Bilayer-preferring lipids generally have a substantial similarity between the surface areas of their headgroups and the cross-sectional area of their acyl chains. The acyl chains of bilayer-preferring lipids generally are in about parallel orientation with respect to each other in bilayers. Bilayer-preferring lipids generally adopt bilayer-compatible structures, and generally are not involved in establishing bilayer defects. The neutral bilayer-preferring lipid can be a phosphatidylcholine, such as egg phosphatidylcholine, or other neutral, bilayer-preferring lipids.

The outermost lipid bilayer of the liposome also comprises a fusion promoting effective amount of an ionizable lipid having a protonatable, cationic headgroup, that is, a headgroup which can accept a proton, and is then positively charged, and which can give up the proton such that is neutral. The ionizable lipid also comprises an unsaturated acyl chain, preferably, two unsaturated acyl chains. The cationic headgroup is preferably an amino group such as a dimethylamino or trimethylamino group, but can also be other groups which can be protonated, and positively charged, and deprotonated, and neutral.

The unsaturated acyl chain is generally nonbilayer preferring. Nonbilayer-preferring acyl chains generally do not adopt conformations in bilayers in which the chains are in parallel orientation. The cross-sectional areas of such acyl chains typically, and unlike bilayer-preferring acyl chains, are not equal to each other and to the headgroup surface area, because, it is believed, of their non-parallel orientation. Bilayers containing nonbilayer-preferring acyl chain-containing lipids generally exhibit a lower $T_M$ or temperature at which the transition from the gel to fluid state occurs, in comparison to bilayers containing bilayer-preferring acyl chain lipids of the same length (number of carbon atoms). It is believed that incorporation of nonbilayer-preferring lipids into bilayers generally increases the tendency of the bilayer to form defects and to have less stability than if bilayer-preferring lipids were used. Such defects are generally believed to be involved in the fusion of lipid bilayers. Without intending in any way to be limited by theory, it is believed that bilayer destabilization, and hence, fusion, requires a substantial imbalance between the size of the headgroup of the fusogenic lipid and the size of area occupied by its acyl chains.

Preferably, the unsaturated acyl chains are oleic acid chains, which are acyl chains having eighteen carbon chains having a double bond between the ninth and tenth carbon atoms. However, the unsaturated acyl chains can be other acyl chains as well, such as those typically having between 12 and 24 carbon atoms and 1–4 double bonds, for example, palmitoleate (16 carbons/1 double bond) or arachidonate (20 carbon atoms/4 double bonds) chains, as long as these generally anchor the lipid in the bilayer and are non-bilayer-preferring. Preferably, the cationic headgroup is an amino group, the unsaturated acyl chain is an oleic acid chain, the ionizable lipid comprises two such chains, and is 1-N,N-dimethylamino dioleoylpropane (AL-1). The AL-1 can be optically active or racemic, that is, an optically inactive mixture of isomers; preferably, the AL-1 is racemic.

Other suitable ionizable lipids are those with titratable headgroups, that is, headgroups which do not have a permanent positive charge, but rather, headgroups which can be protonated and deprotonated in response to changes in the surrounding pH, and non-bilayer preferring acyl chains. These include, but are not limited to: ±-oleoyl-2-hydroxy-3-N,N-dimethylaminopropane (AL-2), asymmetric ±-1,2-diacyl-3-N,N-dimethylaminopropane (AL-3-AL-5) and ±-1, 2-didecanoyl-1-N,N,-dimethyl aminopropane (AL-6). The fusogenic capacity of each of these lipids can be compared, for example, by preparing liposomes with the same amount of each of the lipids and then comparing the relative rates of fusion of the liposomes. Liposome fusion can be monitored by a number of means, for example, by fluorescent probe dilution experiments (see, for example, Example 4 hereinbelow). FIG. 9 presents data comparing the relative fusion rates of liposomes containing the ionizable lipids AL-1, AL-2, AL-3, AL-4, AL-5 and AL-6.

The liposome has a compartment adjacent to its outermost lipid bilayer which comprises an aqueous solution (the "internal aqueous solution") having a first pH. The liposome is suspended in an aqueous solution (the "external aqueous solution") having a second pH. Typically, the liposome is prepared in an aqueous solution, which is both entrapped by the liposome, and in which the liposome is suspended. Accordingly, the internal and external aqueous solutions generally initially have the same composition, and also, the same pH. Their pH is less than the pKa of the ionizable lipid in the liposome's outermost lipid bilayer.

A compound's $pK_a$, that is, its acid dissociation constant, is the pH at which the compound is half-dissociated, that is, the pH at which about half of the molecules of the compound present in solution are deprotonated. $pK_a$ can be defined by the formula: log ([HA]/[H$^+$] [A$^-$]), where HA is the protonated compound and A$^-$ is the deprotonated compound. The Henderson-Hasselbach equatin (pH=$pK_a$+ log ([A–]/HA])) describes the relationship between the pH of a solution and the relative concentrations of the protonated and deprotonated forms of a compound present in solution. At a pH greater than its $pK_a$ in a lipid bilayer, more than half of the ionizable lipid present in the bilayer will be deprotonated, and hence, neutral. Determination of an ionizable lipid's pKa can be accomplished by well known and readily practiced means, for example, by TNS fluorescence titrations.

The ionizable lipid is substantially protonated when the pH of both the internal and external aqueous solutions are less than its $pK_a$ in the bilayer, and is generally about evenly distributed between the inner and outer monolayers of the outermost lipid bilayer, that is, about 50% of the ionizable lipid present is in the inner monolayer, and 50% is in the outer monolayer.

A pH gradient is established across the outermost lipid bilayer by increasing the pH of the external aqueous solution so as to obtain an external aqueous solution with a second pH which is greater than the first pH, and is greater than the $pK_a$ of the ionizable lipid in the bilayer. The protonated, charged ionizable lipid is accumulated in the inner monolayer of the outermost lipid bilayer in response to the pH gradient. "Accumulate," as used herein, means that greater than about 50% of the ionizable lipid present in the outermost bilayer is in its inner monolayer when there is a pH gradient across the bilayer; preferably, between about 75% and about 100%, more preferably, between about 90% and about 100%, and most preferably, about 100% of the protonated ionizable lipid is in the inner monolayer in response to the pH gradient.

For example, in a preferred embodiment of the invention, the ionizable lipid is AL-1. Liposomes can be prepared with AL-1 and, for example, egg phosphatidylcholine (EPC) and cholesterol (Chol), or EPC, Chol and dioleoyl phosphatidylcholine (DOPE). As EPC, Chol and DOPE are neutral lipids, the $pK_a$ of AL-1 in EPC/Chol or EPC/Chol/DOPE bilayers is about 6.7. Accordingly, the first pH, the pH of the internal aqueous solution, is less than 6.7 in connection with AL-1/EPC/Chol or AL-1/EPC/Chol/DOPE liposomes; preferably, the first pH in connection with such AL-1 containing liposomes is about 4.0. Typically, the internal aqueous solution is an aqueous buffer; presently, the preferred aqueous buffer is a citric acid buffer.

The second pH, that is, the pH of the external aqueous solution, is greater than 6.7 when the liposome comprises AL-1/EPC/Chol or AL-1/EPC/Chol/DOPE; preferably, the second pH is about 7.5. However, incorporation of other lipids into AL-1/EPC/Chol or AL-1/EPC/Chol/DOPE liposomal bilayers can affect the pKa of AL-1 therein. Ionizable lipids other than AL-1 can have different pKa's than AL-1. Accordingly, the first and second pH's may vary from the preferred pH values when the composition of the liposome is altered.

When the first pH is less than the ionizable lipid's pKa in the outermost lipid bilayer, the second pH is greater than the pKa, and the ionizable lipid is accumulated in the inner monolayer of the outermost lipid bilayer, the positive charge of the ionizable lipid is substantially absent from the outer monolayer, and is shielded from exposure to the external environment. When administered to animals, positively charged lipid can cause toxic side effects and can promote opsonization, the binding of plasma proteins to the liposome's outer surface, thereby promoting clearance of liposomes from the animal's circulation. Accumulating the positive charge in the inner monolayer minimizes the potential for toxic side effects and for opsonization.

Furthermore, the pH gradient which induces the ionizable lipid to accumulate in the inner monolayer can also be used to load cationic, lipophilic biologically active agents, for example, the anthracycline antineoplastic agent doxorubicin, into the liposomes (see, for example, Bally et al., U.S. Pat. No. 5,077,056, the contents of which are incorporated herein by reference)).

Degradation of the pH gradient leads to an increase of the internal pH above the ionizable lipid's $pK_a$. This leads to substantial deprotonation of the accumulated ionizable lipid. The substantially deprotonated, neutral ionizable lipid is then about evenly distributed between the inner and outer monolayers of the outermost lipid bilayer. The neutral ionizable lipid is "fusogenic" when exposed, in the outer monolayer, to other lipid bilayers, that is, it can promote the fusion of the liposome to the other lipid bilayers. Using an ionizable lipid having a $pK_a$ in the bilayer which is less than about 7 means that the pH gradient can be degraded at physiological pH, for example, in an animal, such that the ionizable lipid is substantially deprotonated and fusogenic. The internal pH of the liposome does not generally need to be raised above physiological pH to induce substantial deprotonation of the ionizable lipid. Ionizable lipid's having $pK_a$'s substantially above physiological pH may not be fusogenic when administered to animals as they may not be substantially deprotonated in the animal.

The ionizable lipid is present in the outermost lipid bilayer in a "fusion promoting effective amount." Fusion of liposomes with other lipid bilayers can be defined as fusion of the outermost lipid bilayer of the liposome with the other lipid bilayer, for example, a cell membrane (see, for example, Huang (1983)). For fusion to occur, the lipids of the outermost lipid bilayer must mix with the lipids of the other lipid bilayer. Without intending in any way to be limited by theory, it is believed that for fusion to occur, the charged headgroups on lipids have to be neutralized, resulting in an effective change in the geometry of the lipids, which gives rise to nonbilayer-preferring structures.

For the purpose of this invention, a "fusion-promoting effective amount" of an ionizable lipid is an amount of the ionizable lipid effective to promote fusion of the liposome to another lipid bilayer when the ionizable lipid is deprotonated and neutral. Fusion-promoting effective amounts of an ionizable lipid are generally effective to form a sufficient degree of defects in a bilayer to promote fusion of the bilayer to another bilayer. Typically, the "fusion promoting effective amount" of the ionizable lipid is an amount sufficient to establish a concentration of the ionizable lipid in the outermost lipid bilayer of from about 1 mole percent to about 20 mole percent. Desirably, the fusion-promoting effective amount of the ionizable lipid is an amount sufficient to establish a concentration of the ionizable lipid in the outermost lipid bilayer of between about 5 mole percent and about 10 mole percent.

The liposome can also comprise a neutral, nonbilayer-preferring lipid. As used herein, a "neutral, nonbilayer-preferring lipid" is an amphipathic lipid having a non-cationic, non-anionic headgroup and nonbilayer-preferring acyl chains. Nonbilayer preferring acyl chains generally are not arranged in parallel orientation in bilayers, and generally do not have similar areas occupied by their headgroup surfaces and a cross-section of their acyl chains. The most favorable packing conformation for such acyl chains is generally in non-bilayer structures. Bilayers containing nonbilayer-preferring lipids generally exhibit a lower $T_m$, or temperature at which the transition from the gel to fluid state occurs, in comparison to bilayers containing bilayer-preferring acyl chain lipids of the same length (number of carbon atoms). Accordingly, nonbilayer preferring lipids generally facilitate a bilayer's transition from the gel to the fluid state, and thereby generally accelerate fusion of the bilayer to another bilayer. In a presently preferred embodiment of the invention, the neutral, nonbilayer-preferring lipid is dioleoyl phosphatidylethanolamine (DOPE).

The liposome can also comprise proteins and other lipids, for example, cholesterol and its derivatives, incorporated into the liposome in amounts, and for reasons, well known to ordinarily skilled artisans, or readily determinable by them without undue experimentation.

The liposome can comprise a biologically active agent, a term that includes traditional pharmaceuticals, and related biologically active compounds or compositions of matter, having biological activity in an animal or on an animal's cells in vitro. Bioactive agents include, but are not limited to: antibacterial agents, antiviral agents, antifungal agents, antiparasitic agents, tumoricidal agents, anti-metabolites, carbohydrates, polypeptides, peptides, proteins, toxins, enzymes, hormones, neurotransmitters, glycoproteins, lipoproteins, immunoglobulins, immunomodulators, vasodilators, dyes, radiolabels, radio-opaque compounds, fluorescent compounds, polysaccharides, cell receptor binding molecules, antiinflammatory agents, mydriatic compounds, local anesthetics, narcotics, anti-glaucomic agents, vitamins, nucleic acids, polynucleotides, nucleosides, nucleotides, MRI and radio contrast agents.

The liposome composition can be administered to animals, preferably mammals, and more preferably, humans, to deliver biologically active agents entrapped in, or associated with, the liposome to the cells of the animal. When the composition is administered to animals, the external aqueous solution is tolerable, that is, substantially non-toxic, to the animals; accordingly, the external aqueous solution is a pharmaceutically acceptable solution or "carrier". Pharmaceutically acceptable carriers are generally selected with regard to the intended route of administration and standard pharmaceutical practice. For parenteral administration or injection via intravenous, intraperitoneal, intramuscular, subcutaneous, or intra-mammary route, sterile solutions of the liposome composition are prepared; the total concentration of solutes may be controlled to render the preparation isotonic. Typical carriers used for parenteral administration include, but are not limited to, aqueous dextrose-containing solutions such as D5W (5% weight by volume dextrose in water) and physiologically acceptable saline solutions. Pharmaceutically acceptable carriers can also include alcohols, gum arabic, benzyl alcohols, gelatin, carbohydrates, such as lactose, amylose or starch, magnesium stearate, talc, silic acid, hydroxy methylcellulose, polyvinyl pyrrolidone, and the like. They can also contain components, for example, preservatioves, anti-oxidants, and the like, in amounts, and for reasons, well within the purview of the ordinarily skilled artisan to determine.

This invention also provides a dehydrated liposome having an outermost lipid bilayer comprising a neutral, non-bilayer-preferring lipid and a fusion-promoting effective amount of an ionizable lipid having a protonatable, cationic headgroup and an unsaturated acyl chain, wherein the ionizable lipid is accumulated in the inner monolayer of the outermost lipid bilayer. Liposomal dehydration can enable the liposomes to be stored for extended periods of time; dehydrated liposomes can then be reconstituted on an as-needed basis. Liposomes can be dehydrated, with freezing, using standard freeze-drying equipment, or its equivalents. Freeze-drying drying is preferably carried out after incorporating one or more protective sugars into liposome preparations in accordance with the procedures described in Schneider et al. (U.S. Pat. No. 4,229,360) and Janoff et al., (U.S. Pat. No. 4,880,635), the contents of which are incorporated herein by reference). The protective sugar can be omitted if the dehydration is conducted without freezing, and sufficient water is left remaining in the liposomal preparation to maintain the integrity of a substantial portion of the liposomal bilayers through the dehydration-rehydration process.

This invention provides a method of controlling the fusion of a liposome to a second lipid bilayer which comprises preparing the liposome in an aqueous solution, wherein the liposome comprises an outermost lipid bilayer comprising a neutral, bilayer-preferring lipid and a fusion-promoting effective amount of an ionizable lipid having a protonatable, cationic headgroup and an unsaturated acyl chain. The liposome also comprises a compartment adjacent to the outermost lipid bilayer which comprises the aqueous solution. The pH of the aqueous solution is less than the $pK_a$ of the ionizable lipid in the outermost lipid bilayer. The pH of the aqueous solution external to the liposome is then increased above the $pK_a$ of the ionizable lipid in the outermost lipid bilayer, so that there is a pH gradient across the outermost lipid bilayer and the ionizable lipid is then accumulated in the inner monolayer of the outermost lipid bilayer in response to the pH gradient. The pH of the internal aqueous medium is increased above the $pK_a$ of the ionizable lipid in the outermost lipid bilayer when fusion of the liposome to the second lipid bilayer is to occur. The liposome can be a unilamellar liposome, preferably a large unilamellar liposome, or a multilamellar liposome, preferably a multilamellar liposome having substantially equal interlamellar solute distribution. The second lipid bilayer is preferably the plasma membrane of a cell, which is preferably a mammalian cell. However, the second lipid bilayer can also be other lipid bilayers, such as a liposomal lipid bilayer or the cell membrane of a bacteria. The pH of the external aqueous solution is generally raised by adding a sufficient amount of a base to the aqueous solution to obtain the desired pH, or by exchanging the external aqueous solution for a second aqueous solution having the desired pH.

The ionizable lipid is present in the outermost lipid bilayer in a "fusion promoting effective amount," that is, an amount effective to promote fusion of the liposome to a second lipid bilayer. Typically, the "fusion promoting effective amount" of the ionizable lipid is an amount sufficient to establish a concentration of the ionizable lipid in the outermost lipid bilayer of from about 1 mole percent to about 20 mole percent. Preferably, the fusion-promoting effective amount of the ionizable lipid is an amount sufficient to establish a concentration of the ionizable lipid in the outermost lipid bilayer of from about 5 mole percent to about 10 mole percent.

When fusion of the liposome to a second lipid bilayer is desired, the liposome's internal pH is raised above the ionizable lipid's $pK_a$ in the bilayer such that the pH gradient is degraded. The protonated/charged ionizable lipid accumulated in the inner monolayer of the outermost lipid bilayer is substantially deprotonated when the pH of the internal aqueous solution adjacent to the bilayer rises above the lipid's pKa in the bilayer. The substantially deprotonated/neutral ionizable lipid is then about evenly distributed in the outermost lipid bilayer, that is, about 50 percent is in the inner monolayer and about 50 percent is in the outer monolayer. The neutral lipid in the outer monolayer can promote fusion to other lipid bilayers. The pH gradient can be degraded by administering the liposome composition to an animal and allowing the gradient to gradually dissipate in the animal as protons stored in the liposome leak into the external environment. As the liposome's internal pH approaches physiological pH, ionizable lipids with $pK_a$'s less than physiological pH are substantially deprotonated. pH gradient degradation can also be accomplished the use of ionophores, for example, nigericin, which facilitate the transport of ions across lipid bilayers, or by the addition of ions, for example, ammonium ions, which can cross lipid bilayers in their neutral form. When the internal pH is raised above its $pK_a$, the charged ionizable lipid is substantially deprotonated; the neutral lipid is distributed about evenly between the inner and outer monolayers of the outermost lipid bilayer.

The liposome used in the method of this invention can comprise a biologically active agent. The second lipid bilayer to which fusion of the liposome is controlled is preferably the plasma membrane of a cell; preferably, the cell is a mammalian cell. Preferably fusion of the liposome to the plasma membrane of the mammalian cell occurs inside the mammal, that is, *in vivo*. Typically, fusion occurs such that the contents of the liposome are delivered to the cytoplasm of the mammalian cell.

Also provided herein is a method of introducing a biologically active agent into a cell, preferably a mammalian cell, which comprises preparing a liposome comprising the biologically active agent in an aqueous solution, wherein the liposome comprises an outermost lipid bilayer comprising a neutral, bilayer-preferring lipid and a fusion-promoting effective amount of an ionizable lipid having a protonatable, cationic headgroup and an unsaturated acyl chain. The aqueous solution, which has a pH less than the $pK_a$ of the ionizable lipid in the outermost lipid bilayer, is both entrapped by the formed liposome, and surrounds the liposome. The liposome also comprises a compartment adjacent to the outermost lipid bilayer which comprises the aqueous solution. The pH of the aqueous solution external to the liposome is then increased above the $pK_a$ of the ionizable lipid in the outermost lipid bilayer, so that there is a pH gradient across the outermost lipid bilayer and the ionizable lipid is accumulated in the inner monolayer of the outermost lipid bilayer in response to the pH gradient. The pH gradient is then degraded, for example, by administering the liposome to an animal or by using an ionophore, when fusion of the liposome to the cell is to occur. The cell is then contacted with the liposome so that the liposome fuses to the cell, whereby the biologically active agent is introduced into the cell.

This invention will be better understood from the following examples. However, those of ordinary skill in the art will readily understand that these Examples are merely illustrative of the invention as defined in the claims which follow thereafter.

EXAMPLES

Example 1

Lipids and Chemicals

Egg phosphatidylcholine (EPC), dioleoyl phosphatidylethanolamine (DOPE), N-(7-Nitro-2,1,3-benzoxydiazol-4-yl)-1,2-dioleoyl-sn-phosphatidyl ethanolamine (NBD-PE) and N-(lissamine rhodamine B sulphonyl)-1,2-dioleoyl-sn-phosphatidylethanolamine (Rh-PE) were obtained from Avanti Polar Lipids (Alabaster, Ala.). Oleic acid, cholesterol (Chol), nigericin, potassium 2-p-toluidinylnapthalene-6-sulphonate (TNS), and all buffers, were obtained from Sigma Chemical Co. (St. Louis, Mo.). 3-N,N-Dimethylamino-1,2-propanediol and oxalyl chloride were purchased from Aldrich Chemical Co. (Milwaukee, Wis.), and 9,10-d2-oleic acid was supplied by MSD Isotopes (Montreal, PQ). Organic solvents were all HPLC grade, and were used without redistillation.

Synthesis of AL-1

This compound was prepared according to the method of Levantis and Silvius (1990). Oleyl chloride was prepared by slowly adding 3 ml (35 mmol) of oxalyl chloride to 1.0 g (3.5 mmol) oleic acid dissolved in 10 ml benzene without stirring at room temperature for 1 hour. After removal of solvent and excess oxalyl chloride under vacuum, the acid chloride was dissolved in 5 ml diethyl ether, and a further 5 ml of ether containing 0.20 g (1.7 mmol) of 3,N,-dimethylamino-1,2-propanediol and 0.15 g pyridine was added. The resulting mixture was stirred at room temperature for 30 minutes before quenching with 1 ml methanol. Solvents were removed under vacuum. The crude product was dissolved in 50 ml hexane and washed with 2×25 ml 0.1M sodium chloride. Drying over anhydrous sodium sulfate, and removal of hexane under vacuum gave a slightly yellow oil. Column chromatography on silica gel (70–230 mesh), wherein elution was with ethyl acetate, gave 0.92 g (84%) of pure product (TLC, Rf=0.5). 200 MHz 1H-NMR (CDCl$_3$), δ ppm from TNS (J-coupling, integration): 5.3 (dd, 4H), 5.1 (m, 1H), 4.0 (dd, 1 h), 2.4 (dd, 2H), 2.2 (s, 6H), 2.0–0.8 (m, 62H). This procedure was also used to prepare the deuterated analog rac-1-N,N-dimethylamino-2,3-bis(9,10-dideuteriooleoyl)propane (AL-1-d$_4$) and ±-1,2-didecanoyl-1-N,N,-dimethyl-aminopropane (AL-6).

Synthesis of ±-oleoyl-2-hydroxy-3-N,N-dimethylaminopropane (AL-2) and Asymmetric ±-1,2-diacyl-3-N,N-dimethylaminopropane (AL-3–AL-5)

Oleoyl chloride (3.4 mmoles), prepared as described above, was dissolved in 5 ml THF, and added to a five-fold excess of 3-N,N-dimethylamino-1,2-propanediol (2.0 g, 17 mmoles) and 0.15 g pyridine in 25 ml THF at 0 deg. C. Crude 1-monooleoyl-2-hydroxy-3-N,N-dimethylamino propane (AL-2) was isolated, and purified by column chromatography on silica gel using ethylacetate/methanol (3:1) as eluent (R$_f$ 0.4). Subsequent acylation with one equivalent of acetyl chloride, butyryl chloride or decanoyl chloride, with reaction conditions produced AL-3, AL-4 and AL-5, respectively.

Preparation of LUVs

Liposomal liposomes were prepared according to known methods by drying chloroform solutions of lipids under nitrogen, followed by removal of residual solvent under high vacuum for one hour. The resulting lipid films were hydrated by vortex-mixing with appropriate buffers to produce multilamellar liposomes (MLVs). Five freeze-thaw cycles were used to achieve homogeneous mixtures. The MLVs were extruded ten times through two 100 nm pore-size polycarbonate filters to produce large unilamellar liposomes (see, for example, Bally et al., U.S. Pat. No. 4,885,172; Cullis et al., U.S. Pat. No. 4,975,282; Cullis et al., U.S. Pat. No. 5,008,050; Loughrey et al., U.S. Pat. No. 5,059,421).

Example 2

Determination of Lipid Asymmetry by TNS Fluorescence

The transport of AL-1 to the inner monolayer of liposomes was demonstrated by TNS fluorescence using a procedure adopted from Eastman et al. (1991). The fluorescence of TNS as a function of AL-1 concentration was first calibrated using LUVs containing 0, 2.5, 5.0, 7.5 and 10.0 mole % AL-1 in EPC/Chol (55:45), 5 mM total lipid, in 20 mM HEPES, 150 mM NaCl, pH 7.5. Aliquots of 90 µl were added to 2.9 ml of 20 mM HEPES, 150 mM NaCl, 5 µM TNS, pH 7.5, and fluorescence was monitored over 5 minutes. Liposomes prepared with 10 mole % AL-1, internal pH 7.5, as described above, were also used for comparison.

Figure 1A:
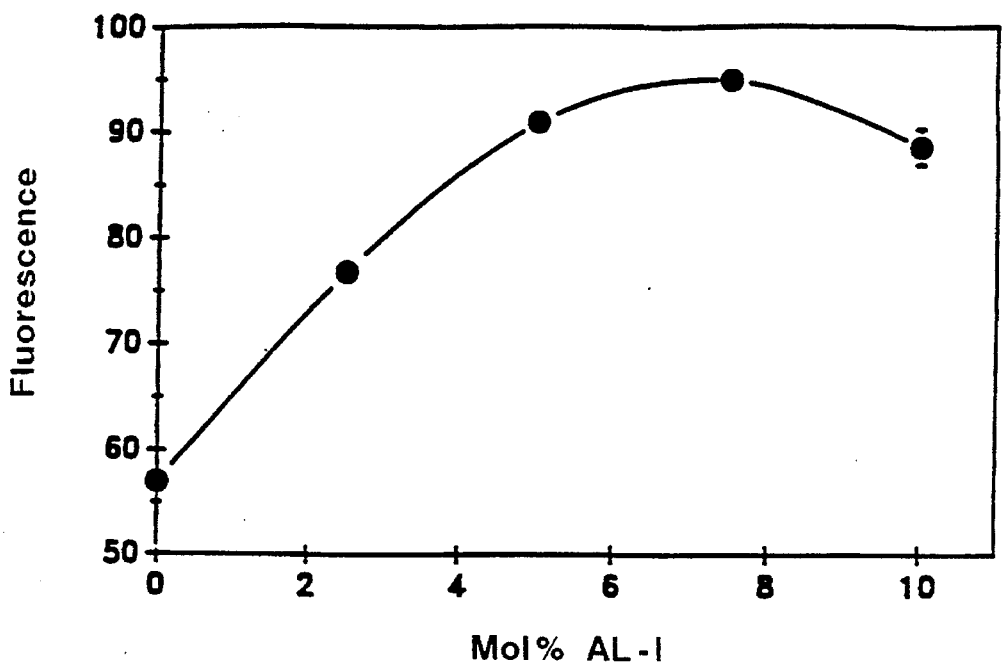
FIG. 1. (A) Calibration of TNS fluorescence for EPC/Chol liposomes containing 0–10 mole % AL-1. X-axis.

Results are presented in FIG. 1. The effect of a pH gradient on the transbilayer distribution of AL-1 was demonstrated by monitoring the surface charge of AL-1-containing liposomes, by TNS fluorescence, after the imposition of a pH gradient. For concentrations of 0–5 mole % AL-1, a steady increase in fluorescence was seen as surface charge increased (see FIG. 1A). However, at higher concentrations, the fluorescence levels off and begins to decrease. This effect was not observed with liposomes containing AL-1 in EPC without cholesterol, where fluorescence increases linearly for up to 20 mole % AL-1. This was an early indication that liposomes containing 10 mole % AL-1 in EPC/Chol (55:45) are aggregated, giving decreased liposomal surface area for TNS interaction.

Figure 1B:
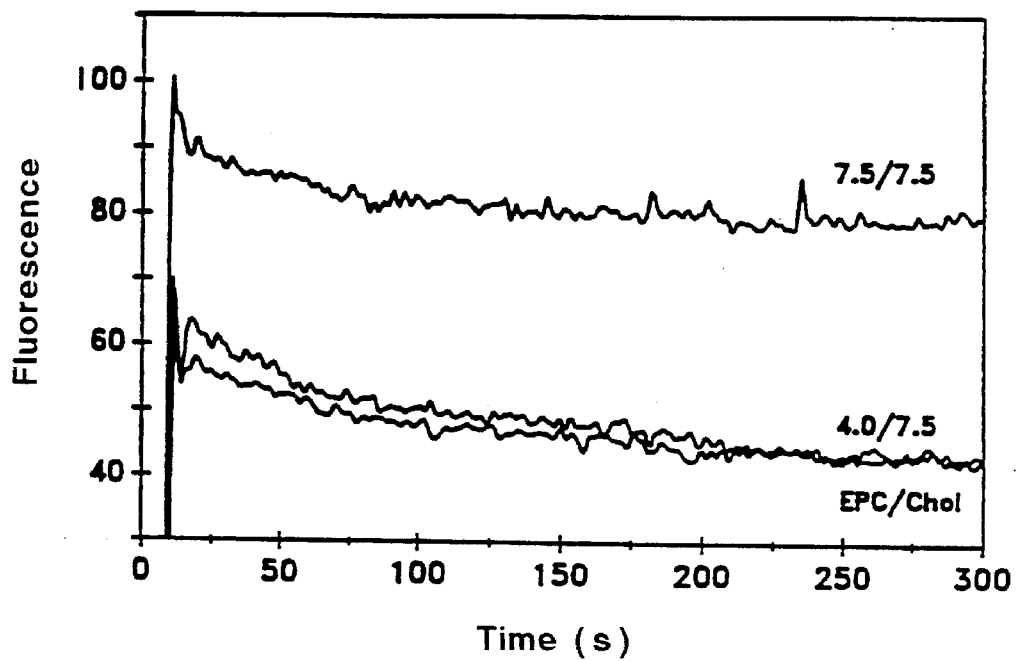

The effect of a pH gradient on TNS fluorescence with 10 mole % AL-1 in EPC/Chol (55:45) is illustrated in FIG. 1B The curve at the top of the figure gives fluorescence as a function of time in the absence of a gradient, internal and external pH 7.5, with 10 mole % AL-1. The bottom curve is for a vesicle, internal pH 4 and external pH 7.5, but without AL-1. The slow decreases in fluorescence observed in these curves is a result of photobleaching of TNS during the course of the experiments. The remaining curve shows that for 10 mole % AL-1 with a gradient, the majority of the increased surface charge of the liposomes, and therefore, AL-1, was very quickly lost from the outer monolayer. After four minutes, the fluorescence was equal to that of the EPC/Chol liposomes, indicating that virtually all of the AL-1 had moved to the inner monolayer. The rapid movement of the AL-1 across the bilayer is advantageous for its use in controlling fusion. Similar behavior was observed for AL-2–AL-6 (see FIG. 9).

Example 3

Determination of Ionizable Lipid pK$_a$'s

To determine the pH at which AL-1 in liposomal membranes loses its charge, LUVs containing 0 and 10 mole % AL-1 and EPC/Chol (55:45) were prepared in 5 mM HEPES, 5 mM ammonium acetate at pH 4.0. Preparations were diluted to 0.25 mM total lipid in 5 mM HEPES, 5 mM ammonium, 2 µM TNS at pHs ranging from 3.0 to 10.0 The pH across the vesicle membranes was rendered equal by adding nigericin to a final concentration of 0.01 µM. The TNS fluorescence at each pH value was determined under the conditions given above.

Results are presented in FIG. 2, which shows TNS fluorescence at various pH values in the absence of a pH gradient. The data clearly indicates a $pK_a$ of 6.7 for the conjugate acid of AL-1. A comparison of results derived from similar pH titration curves for the synthetic aminolipids AL-2–AL-6 is given in Table 1 (see below). The effects of chemical structure on the acid-base characteristics of the amines when incorporated into liposomes are manifested as changes in the $pK_a$ values observed, and in the fraction of aminolipid species remaining charged at pH 7.5. These changes can stem from the depth of penetration of the amine headgroup into the lipid bilayer, as influenced by the relative hydrocarbon chain length and the polarity of the headgroup. Compound AL-2, having only a single oleoyl chain and an unsubstituted hydroxy group, has a $pK_a$ of about 7.57. Esterification of the hydroxyl at the 2 position with acetate, to give AL-3, reduces the $pK_a$ to 6.79, and the fraction of neutral species at pH 7.5 is 16%, compared with 11% for AL-1. The remaining compounds, AL-4, AL-5 and AL6, also have sufficient hydrocarbon content to have pKa's and relative charges at pH 7.5, which approach those for AL-1.

TABLE 1

Apparent Acid Dissociation Constants ($pK_a$) and Percent
of Charged Species at pH 7.5 for Aminolipids AL-1–AL-6*

| Aminolipid | Apparent $pK_a$ | % Charged at pH 7.5 |
|---|---|---|
| AL-1 | 6.58 | 11 |
| AL-2 | 7.57 | 54 |
| AL-3 | 6.79 | 16 |
| AL-4 | 6.66 | 13 |
| AL-5 | 6.73 | 14 |
| AL-6 | 6.81 | 17 |

*The data were derived from TNS fluorescence titrations. Curves for each aminolipid were fitted to the Henderson-Hasselbach equation by iteratively varying $pK_a$ and maximum and minimum fluorescence.

Example 4

Lipid-Mixing Fusion Assay

Fusion was monitored by the decrease in resonance energy transfer (RET) resulting from fluorescent probe dilution, as described by Struck et al. (1981). LUVs were prepared by 0 and 10 mole % AL-1 in EPC/Chol (55:45) and EPC/DOPE/Chol (30:25:45)in 300 mM citrate pH 4.0. The external buffer was 20 mM HEPES (150 mM NaCl, pH 7.5). Liposomes containing 0.7 mole % of both NDB-PE and Rh-PE for each lipid composition, at each of the AL-1 concentrations, were also prepared. Labeled and unlabeled liposomes were mixed in a 1:3 ratio, and diluted to 0.2 mM total lipid. External buffer was exchanged for 300 mM sucrose, 1 mM citrate, pH 4.0, on Sephadex G-25 columns before diluting preparations to 10 mM lipid. For fusion assays, 20 μl of fluorescently labeled liposomes, and 60 μl unlabeled liposomes, were added to 3.92 ml of 20 mM HEPES, 150 mM NaCl, pH 7.5. After 5 min. of incubation at room temperature, a 3 ml aliquot was added to a cuvette, and the fluorescence was monitored over 5 minutes. Excitation and emission wavelengths were 465 and 535 nm, respectively, and an emission 530 nm cutoff filter was used. To dissipate the gradient and induce fusion, ammonium acetate was added to a final concentration of 100 mM at 30 seconds. The percent change in fluorescence (% $F/F_{max}$) was determined by assigning zero fluorescence ($F_0$) to a trace with no ammonium acetate added and $F_{max}$ to a trace measured after adding 100 μl of 25 mM Triton X-100, so that:

$$\% \ (F/F_{max}) = 100 \times ((F-F_0)/(F_{max}-F_0))$$

To study the effects of varying the AL-1 concentration (0–20 mole %) on the fusion liposomes comprising EPC/Chol (55:45) were prepared, with, and without, 0.5 mole % each of NBD-PE and Rh-PE, using an internal pH 4.0, 300 mM sodium citrate buffer, and an external 20 mM HEPES buffer (150 mM NaCl, pH 7.5). The labeled and unlabeled liposomes were mixed in a 1:3 ratio and diluted to 0.20 mM total lipid. The pH gradient was dissipated by the addition of ammonium acetate to a final concentration of 100 mM at 30 seconds.

To study the effects of varying the DOPE concentration on the fusion rates of AL-1-containing liposomes, LUVs were prepared with EPC/DOPE/Chol 55-X:X-45, X=0, 5, 10, 15, 20), 10 mole percent AL-1, with or without 0.5 mole % each of NBD-PE and Rh-PE, an internal pH 4.0, 300 mM sodium citrate buffer, and an external 20 mM HEPES buffer (150 mM NaCl, pH 7.5).

To study the effect of aminolipid structure on the fusion of EPC/Chol/DOPE liposomes (35:20:45) liposomes were prepared with 5 mole % of the indicated aminolipid (AL-1–AL-6), an internal pH 4.0, 300 mM sodium citrate buffer, and an external 20 mM HEPES buffer (150 mM NaCl, pH 7.5). Fusion assays were carried out as described above.

Results are presented in FIGS. 3, 4, 6, 7 and 9. The pH gradient across the membranes of liposomes with acidic interiors can be dissipated by ionophores, such as nigericin, or by the addition of ammonium ions which can cross the membrane in the form of neutral ammonia to raise the internal pH. For LUVs in which AL-1 is exclusively on the inner monolayer, loss of the pH gradient would be expected to give redistribution of the AL-1 between the monolayers. Under conditions where AL-1 is deprotonated and bilayer-unstable, liposomal fusion can occur.

Membrane fusion was monitored by a loss in RET between the fluorescently labeled lipids NBD-PE and Rh-PE. When liposomes containing both of these labels fuse with unlabeled liposomes, the resulting dilution of the fluorescent probes gives increased fluorescence for NBD-PE. Appreciable exchange of these labeled lipids between liposomes does not appear to occur even in aggregated systems, and fluorescence increases only upon mixing of membrane lipids.

The use of the fluorescent probe dilution assay to demonstrate fusion in LUVs containing 10 mole % AL-1 is depicted in FIGS. 3 and 4. Unlabeled and labeled liposomes (3:1) comprising EPC/Chol (55:45) with no AL-1 showed no increase in fluorescence upon dissipation of the pH gradient. A small decrease in fluorescence was observed due to the addition of the ammonium solution. Similar liposomes containing 10 and 20 mole % AL-1 gave a rapid increase in fluorescence which leveled out quickly at a value of $\Delta F/\Delta F_{max}$ near 3%. This represents only a limited amount of the total possible lipid mixing which for 3:1 mixtures of unlabeled and labeled liposomes should give a $\Delta F/\Delta F_{max}$ of 80%, as determined by preparing liposomes with the fluorescent labels at one quarter of the normal concentration (0.18 mole %). The low fluorescence increase observed indicates that, while AL-1 can induce pH gradient-controlled fusion in EPC/Chol liposomes, its ability to do so is limited. For AL-1 concentrations greater than about 20 mole %, in EPC/Chol liposomes, rapid and complete liposome aggregation was observed following extrusion.

The fusogenic nature of EPC/Chol liposomes can be increased by including dioleoyl phosphatidylethanolamine (DOPE) in the lipid bilayer. FIG. 3 shows fluorescent traces demonstrating the effect of 10 mole % AL-1 on the fusion of EPC/DOPE/Chol (30:25:45). Without the aminolipid, there was very little evidence of fusion when the pH gradient was dissipated by ammonium acetate. When AL-1 was included, however, $\Delta F/\Delta F_{max}$ increased to nearly 10% over 5 minutes and continued to rise over 15 minutes. This result demonstrates the usefulness of AL-1 in controlled fusion and illustrates the importance of lipid composition to the extent of fusion observed. Results of fusion assays for EPC/DOPE/Chol liposomes containing 10 mole % AL-1, where increasing levels of DOPE replace EPC, are shown in FIG. 6. Increasing fusion rates were evident with increasing DOPE concentrations up to lipid ratios of 35:20:45 (EPC/DOPE/Chol, mole/mole). This formulation gave a $\Delta F/\Delta F_{max}$ of greater than 5% after 5 minutes. However, at this level of DOPE, some aggregation of liposomes was observed at low pH. Higher DOPE levels gave rapid aggregation.

The best rates of fusion observed when the AL-1 concentration was reduced to about 5 mole % in EPC/DOPE/Chol (35:20:45) liposomes are shown in FIG. 7. At pH 4.0 with this formulation, stable liposomes were prepared, and these remained stable when the external pH was increased to 7.5. Dissipation of the pH gradient results in a nearly linear increase in $\Delta F/\Delta F_{max}$ over the first 5 minutes to a value greater than 10%. Although the rate of fusion decreased with time, fusion continued for the duration of the 15-minute assay.

A comparison of the fusogenic capacity of the aminolipids AL-1-AL-6 was made by assaying for fusion with liposomes containing 5 mole % of each aminolipid in EPC/DOPE/Chol liposomes (35:20:45). Results are shown in FIG. 9 AL-2, which has single oleoyl chain, gives little increase in liposome fusion in comparison with liposomes not containing aminolipid. It is believed that the lack of fusogenic activity may result from the relative high $pK_a$ of AL-2 in such bilayers, and from the relatively small area in the bilayer occupied by the single acyl chain of AL-2. Without intending in any way to be limited by theory, it is believed that bilayer destabilization, and hence, fusion, requires a substantial imbalance between the size of the headgroup of the fusogenic lipid and the size of area occupied by its acyl chains. Liposomes containing AL-3 exhibit a substantially greater fusion rate, and lengthening AL-3's second chain to butyryl (AL-4) or decanoyl (AL-%) gives further increases in the fusion rate, with rates approaching those achieved with AL-1—containing liposomes. Incorporation of compound AL-6 with two decanoyl chains into liposomes gave only limited mixing, despite its comparatively low $pK_a$.

Example 5

$^2$H-NMR Spectroscopy

Freeze-thawed MLVs of 10 mole % AL-1-d$_4$ in EPC/Chol (55:45) were prepared as described above in 100 mM ammonium acetate at pH 4.0 and pH 7.5 in deuterium-depleted water. Sample concentrations were approximately 150 mM total lipid. Broad line quadrupole spectra were recorded on a Bruker MSL200 spectrometer at 30.7 MHz, using a spin-echo sequence with a 5.3 µs 90° pulse and a 200 ms repeat delay. Temperature was maintained at 20° C. with a liquid nitrogen flow system. The free induction decay (FID) signal was accumulated overnight (approximately 280,000 scans) for the sample at pH 4.0, while comparable signal-to-noise with the pH 7.0 sample was achieved with approximately 770 scans. FIDs were transformed using 100 Hz line-broadening.

Example 6

$^2$H-NMR and $^{31}$P-NMR Spectroscopy

Freeze-thawed MLVs containing 5 mole percent AL-1-d$_4$ in EPC/Chol (55:45) were prepared in 20 mM HEPES, 20 mM ammonium acetate, 150 mM NaCl, pH 4.0 and pH 7.5, using deuterium-depleted water. Sample concentrations were approximately 200 mM total lipid. $^2$H-NMR broadline spectra were recorded at 46.175 MHz, on a home-built 300 MHz spectrometer using a 5 µs 90° pulse, 50 µs interpulse spacing, 30.5 µs ring-down delay, and a 300 ms repetition time. A quadrupole echo sequence with eight-step phase cycling was used to accumulate 200,000 scans. The resulting free induction decay (FID) was transformed with 100 Hz line-broadening. High resolution $^{31}$P spectra were recorded at 81 MHz on a Bruker MSL200 spectrometer, using a 2.8 µs pulse and 30 s repeat. Temperature was maintained at 23 degrees Celsius with a liquid nitrogen flow system. The FID was accumulated over 1000 scans, and transformed with 50 Hz line broadening.

NMR spectroscopy results are presented in FIGS. 5 and 8. The limited degree of fusion observed with AL-1 in EPC/Chol (55:45) liposomes indicated that, although the deprotonated form of the aminolipid was not stable in the bilayer, this instability did not confer a permanent non-bilayer structure to the lipid membrane. This may have been a result of the limited solubility of the neutral amine in the bilayer. Separate crystalline or fluid domains of AL-1 may form before extensive fusion can occur.

The phase behavior of AL-1 was investigated by the synthesis of a deuterium chain-labeled analog, AL-1-d$_4$, which was incorporated into MLVs at a concentration of 10 mole % EPC/Chol (55:45). The use of MLVs in this experiment avoids the rapid tumbling of LUVs on the NMR time scale. In FIG. 4, the $^2$H-NMR spectrum at pH 4.0 shows quadrupolar splittings for the chain-labeled positions of AL-1-d$_4$, with the expected magnitude for lipid in the bilayer. At pH 7.5, the bilayer signal is no longer present, and a strong isotropic peak appears in the middle of the spectrum. This is strong evidence that AL-1 exists in separate fluid domains at pH 7.5. The limited degree of fusion observed upon neutralization and redistribution of AL-1 is likely to be a result of the formation of these domains.

Figure 8A:
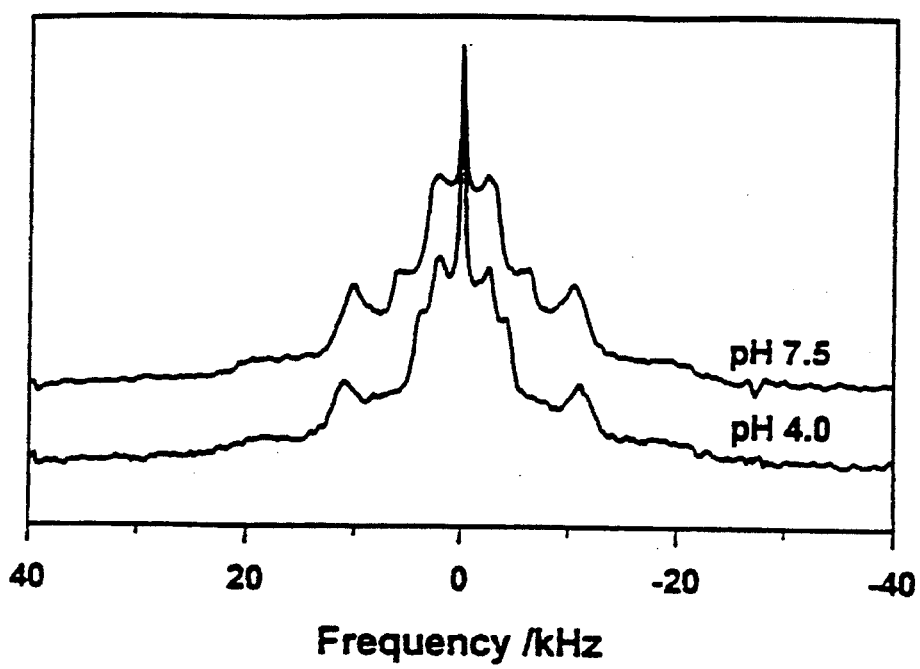

The $^2$H spectrum at pH 4.0 in FIG. 8A shows quadrupolar deuterium splittings in the range expected for oleoyl chains on a lipid incorporated into a lipid bilayer. In the sample prepared at pH 7.5, the bilayer persists, although there is a decrease in quadrupolar splittings, which may correlate with less bilayer order. In addition, there is a distinct signal with a splitting of about 12 kHz, which is believed to arise from the portion of the aminolipid which is in the H$_{II}$ phase. The appearance of this signal is therefore consistent with destabilization of the bilayer leading to membrane fusion.

Figure 8B:
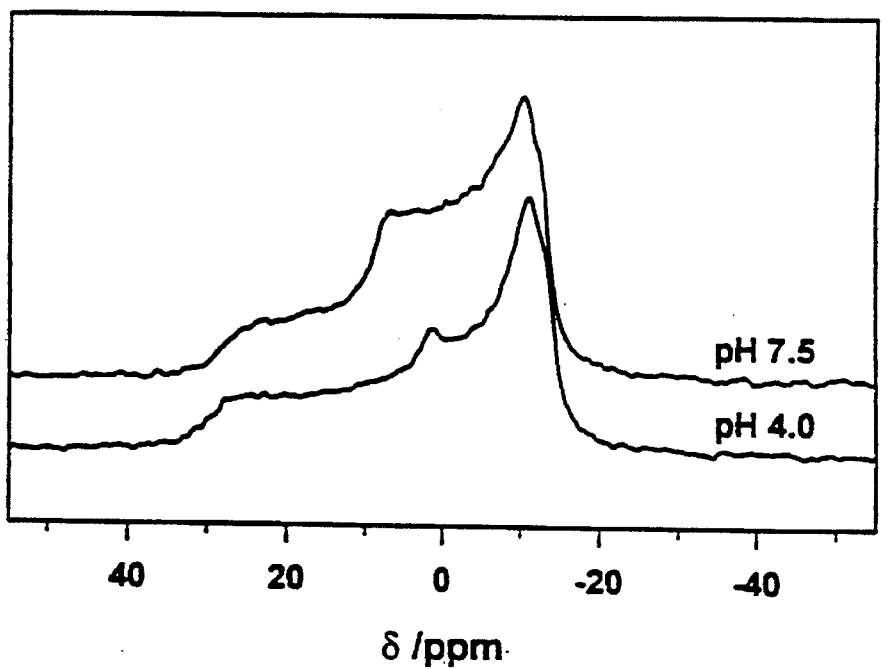

The accompanying changes in the phase behaviors of the phospholipids EPC and DOPE are evident in the $^{31}$P-NMR spectra shown in FIG. 8B. A typical bilayer signal, with an upfield peak and a downfield shoulder, was observed for the pH 4.0 preparation. For the pH 7.5 preparation, the downfield signal is reduced slightly, and an H$_{II}$ signal is seen as a more intense downfield shoulder.

Example 7

Freeze-Fracture Electron Microscopy

LUVs consisting of 10 mole % in either EPC/Chol (55:45) or EPC/DOPE/Chol (30:25:45) were prepared as above in 300 mM sodium citrate at pH 4.0 with a total lipid concentration of 150 mM. External buffer was exchanged for 1 mM citrate, 300 mM sucrose, pH 4.0, on Sephadex G-25 columns. To 200 µl of each preparation was added 50 µl of 500 mM ammonium acetate, pH 7.5. Samples were maintained at room temperature for 30 minutes before preparing platinum/carbon replicas (see Fisher and Branton (1974)).

Example 8

Freeze-Fracture Electron Microscopy

LUVs consisting of 5 mole % in EPC/DOPE/Chol (30:25:45) liposomes were prepared as above in 300 mM sodium citrate at pH 4.0 with a total lipid concentration of 100 mM. External buffer was exchanged for 1 mM citrate, 300 mM sucrose, pH 4.0, on Sephadex G-25 columns before diluting the preparations to approximately 10 mM lipid with 20 mM HEPES, 150 mM NaCl, pH 7.5. After removal of a control sample, the pH gradient was dissipated by addition of 3 mM ammonium acetate, pH 7.5, to a final concentration of 100 mM. Platinum/carbon replicas were prepared (see Fisher and Branton (1974)) for samples at 4, 15 and 30 minutes after dissipation of the gradient, as well as for a control with the pH gradient present.

What is claimed is:

1. A liposome composition comprising:
    (a) a unilamellar liposome having:
        (i) a bilayer which comprises a bilayer forming phosphatidylcholine and between about 1 mole percent and about 20 mole percent of a fusogenic lipid selected from the group consisting of 1-N,N-dimethylamino dioleoyl propane, 1-oleoyl-2-hydroxy-3-N,N-dimethylamino propane, 1,2-diacyl-3-N,N-dimethylamino propane and 1,2-didecanoyl-1-N,N,-dimethylamino propane; and
        (ii) an internal compartment comprising an aqueous solution; and
    (b) an aqueous solution external to the liposome,
wherein the pH of the internal aqueous solution is less than the pKa of the fusogenic lipid in the bilayer and the pH of the external aqueous solution is greater than the pKa of the fusogenic lipid in the bilayer,
    whereby there is a pH gradient across the bilayer, and
    whereby the fusogenic lipid is accumulated in the bilayer's inner monolayer.

2. The liposome composition of claim 1, wherein the unilamellar liposome is a large unilamellar liposome.

3. The liposome composition of claim 1, wherein the aqueous solution is an aqueous buffer.

4. The liposome composition of claim 3, wherein the aqueous buffer has a pH of about 4.0.

5. The liposome composition of claim 4, wherein the aqueous buffer is a citrate buffer.

6. The liposome composition of claim 1, wherein the fusogenic lipid comprises from about 5 mole percent to about 10 mole percent of the bilayer.

7. The liposome composition of claim 1, wherein the fusogenic lipid is 1-N,N-dimethylamino dioleoyl propane.

8. The liposome composition of claim 1, wherein the bilayer further comprises a lipid comprising a neutral headgroup and at least one unsaturated acyl chain.

9. The liposome composition of claim 8, wherein the lipid is dioleoyl phosphatidylethanolamine.

10. The composition of claim 1, wherein the liposome comprises a biologically active agent.

11. The liposome composition of claim 10, wherein the biologically active agent is a nucleic acid, an antimicrobial agent, an anticancer agent or an anti-inflammatory agent.

12. The liposome composition of claim 1, wherein the external aqueous solution is a pharmaceutically acceptable aqueous solution.

13. A dehydrated unilamellar liposome having a bilayer comprising a bilayer-forming phosphatidylcholine and between about 1 mole percent and about 20 mole percent of a fusogenic lipid selected from the group consisting of 1-N,N-dimethylamino dioleoyl propane, 1-oleoyl-2-hydroxy-3-N,N-dimethylamino propane, 1,2-diacyl-3-N,N-dimethylamino propane and 1,2-didecanoyl-1-N,N,-dimethylamino propane, wherein the fusogenic lipid is accumulated in the bilayer's inner monolayer.

14. A method of controlling the fusion of a liposome to a cell membrane which comprises:
    (a) preparing the liposome with a bilayer-forming phosphatidylcholine, a fusogenic lipid selected from the group consisting of 1-N,N-dimethylamino dioleoyl propane, 1-oleoyl-2-hydroxy-3-N,N-dimethylamino propane, 1,2-diacyl-3-N,N-dimethylamino propane and 1,2-didecanoyl-1-N,N,-dimethylamino propane, and an aqueous solution having a pH that is less than the fusogenic lipid's pKa in the bilayer, so that the fusogenic lipid comprises from about 5 mole percent to about 20 mole percent of the bilayer and the aqueous solution is both internal and external to the resulting liposome;
    (b) increasing the pH of the aqueous solution external to the liposome above the pKa of the fusogenic lipid in the bilayer, whereby there is a pH gradient across the bilayer and whereby the fusogenic lipid is accumulated in the bilayer's inner monolayer; and
    (c) causing the pH gradient to decay such that the pH of the internal aqueous solution is greater than the pKa of the fusogenic lipid in the bilayer.

15. The method of claim 14, wherein the liposome comprises a biologically active agent.

16. The method of claim 14, wherein the cell is a mammalian cell.

17. The method of claim 14, wherein the liposome is administered to the animal after step (b).

\* \* \* \* \*